US012708516B2

(12) United States Patent
Taylor

(10) Patent No.: US 12,708,516 B2
(45) Date of Patent: Aug. 18, 2026

(54) IMPLANT

(71) Applicant: Aurora Medical Limited, Chichester (GB)

(72) Inventor: Andrew Clive Taylor, Chichester (GB)

(73) Assignee: AURORA MEDICAL LIMITED, Chichester (GB)

( * ) Notice: Subject to any disclaimer, the term of this patent is extended or adjusted under 35 U.S.C. 154(b) by 1051 days.

(21) Appl. No.: 17/779,810

(22) PCT Filed: Nov. 26, 2020

(86) PCT No.: PCT/GB2020/053019

§ 371 (c)(1),
(2) Date: May 25, 2022

(87) PCT Pub. No.: WO2021/111107

PCT Pub. Date: Jun. 10, 2021

(65) Prior Publication Data

US 2023/0000629 A1 Jan. 5, 2023

(30) Foreign Application Priority Data

Dec. 2, 2019 (GB) ..................................... 1917592
Oct. 23, 2020 (GB) ..................................... 2016877

(51) Int. Cl.
*A61F 2/24* (2006.01)
*A61F 2/30* (2006.01)
*A61F 2/42* (2006.01)

(52) U.S. Cl.
CPC ...... *A61F 2/30756* (2013.01); *A61F 2/30771* (2013.01); *A61F 2/42* (2013.01);
(Continued)

(58) Field of Classification Search
CPC .. A61F 2002/30581; A61F 2002/30563; A61F 2/3872; A61F 2002/4243; A61F 2/30756
See application file for complete search history.

(56) References Cited

U.S. PATENT DOCUMENTS 4,467,479 A 8/1984 Brody
4,919,668 A * 4/1990 Rosenbaum .......... A61F 2/3099 623/8

(Continued)

FOREIGN PATENT DOCUMENTS

DE 102019114314 A1 * 12/2020 ........... A61F 2/4261
EP 2904990 8/2015

(Continued)

OTHER PUBLICATIONS

International Search Report and Written Opinion issued on Feb. 22, 2021 in International Application No. PCT/GB2020/053019.

*Primary Examiner* — Alvin J Stewart
(74) *Attorney, Agent, or Firm* — Billion & Armitage

(57) ABSTRACT

The present invention is directed to a hinge joint implant (40) configured to fit in a joint cavity and which can comprise, when in situ, an at least hemi-spherocylindrical configuration, and further a hinge joint implant configured to fit in a joint cavity wherein the implant can extend around the sides of a joint component which may be a bone and/or cartilage. The invention further provides the use of a hinge joint implant according for treating arthritis, and/or torn cartilage, and a method for manufacturing a hinge joint implant from one or more pieces.

18 Claims, 10 Drawing Sheets

Figure 3:
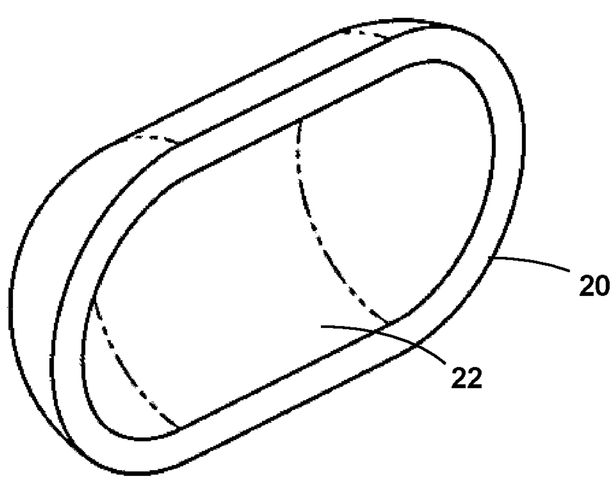

(52) U.S. Cl.
CPC ............... *A61F 2002/30324* (2013.01); *A61F 2002/30471* (2013.01); *A61F 2002/30581* (2013.01)

(56) References Cited

U.S. PATENT DOCUMENTS 5,290,314 A * 3/1994 Koch .................... A61F 2/4241 623/21.16
5,549,679 A * 8/1996 Kuslich ............. A61B 17/7098 606/279
5,674,295 A * 10/1997 Ray ........................ A61F 2/442 623/17.12
5,928,284 A * 7/1999 Mehdizadeh ......... A61F 2/4425 606/279
5,984,971 A * 11/1999 Faccioli ................ A61F 2/4241 623/21.11
6,051,751 A * 4/2000 Sioshansi ................ A61L 27/50 623/20.11
6,066,154 A * 5/2000 Reiley .................. A61B 10/025 606/94
6,146,422 A * 11/2000 Lawson .................. A61F 2/442 623/17.11
6,352,560 B1 * 3/2002 Poeschmann ......... A61F 2/4241 623/21.16
6,632,235 B2 * 10/2003 Weikel ............... A61B 17/7258 606/198
7,670,377 B2 * 3/2010 Zucherman ........... A61F 2/4425 623/17.15
7,862,617 B2 * 1/2011 Lamprich ............. A61F 2/4611 623/17.16
8,632,601 B2 * 1/2014 Howald ................ A61F 2/4603 623/22.14
8,986,311 B2 * 3/2015 Boudreault ........ A61B 17/3421 606/90
9,662,218 B2 * 5/2017 Grotz .................. A61L 27/3817
9,808,345 B2 * 11/2017 Grotz ........................ A61F 2/32
10,307,258 B2 * 6/2019 Grotz .................... A61F 2/3859
10,426,453 B2 * 10/2019 Kaiser .................. A61B 17/025
12,035,902 B2 * 7/2024 Nikolchev ........... A61B 17/025
2003/0229372 A1 * 12/2003 Reiley ................... A61F 2/4601 606/192
2004/0133280 A1 * 7/2004 Trieu ...................... A61F 2/442 623/17.11
2004/0143334 A1 * 7/2004 Ferree ..................... A61F 2/442 623/17.15
2004/0236425 A1 * 11/2004 Huang .................... F16F 13/08 623/17.12
2004/0260396 A1 * 12/2004 Ferree ....................... A61F 2/28 623/20.15
2004/0267375 A1 * 12/2004 Friedrichs ................. A61F 2/32 623/22.18
2005/0171604 A1 * 8/2005 Michalow ............... A61L 27/04 623/20.28
2007/0050033 A1 * 3/2007 Reo .................... A61B 17/7062 623/17.13
2009/0076605 A1 * 3/2009 Linares .................. A61B 17/72 623/14.12
2009/0306778 A1 * 12/2009 Marvel ................. A61F 2/4618 606/191
2010/0023126 A1 1/2010 Grotz
2010/0145454 A1 * 6/2010 Hoffman ................. A61F 2/447 623/17.11
2010/0241234 A1 * 9/2010 Linares ................. A61L 27/502 623/18.11
2010/0292798 A1 * 11/2010 Maestretti ............... A61F 2/441 623/17.12
2011/0288642 A1 * 11/2011 Forsell .................. A61F 2/3872 623/14.12
2011/0295370 A1 * 12/2011 Suh .................... A61B 17/7065 623/17.12
2012/0123553 A1 * 5/2012 Sidebotham .......... A61F 2/3601 623/18.11
2012/0316645 A1 * 12/2012 Grotz .................. A61F 2/30756 623/14.13
2013/0018479 A1 * 1/2013 Grotz .................. A61F 2/30756 623/22.14
2013/0066436 A1 * 3/2013 Desa ..................... A61F 2/4241 29/592
2013/0116794 A1 * 5/2013 Shohat .................. A61F 2/4081 623/19.11
2014/0128974 A1 * 5/2014 Bromer ............... A61F 2/30721 623/14.12
2014/0316526 A1 * 10/2014 Grotz .................. A61F 2/30756 623/20.35
2014/0343675 A1 * 11/2014 Vanleeuwen ....... A61F 2/30756 623/14.12
2017/0007410 A1 * 1/2017 Sojka ........................ A61F 2/34
2018/0221161 A1 * 8/2018 Feffery ................. A61F 2/4425
2021/0178019 A1 * 6/2021 Abboud .............. A61L 27/3633
2021/0205068 A1 * 7/2021 Shulock ................ A61F 2/0811
2023/0320862 A1 * 10/2023 Link ..................... A61F 2/4241 623/21.15
2024/0122721 A1 * 4/2024 Marnay ................... A61F 2/442

FOREIGN PATENT DOCUMENTS

WO WO-0074606 A1 * 12/2000 ......... A61B 17/1757
WO 2012096997 7/2012

* cited by examiner

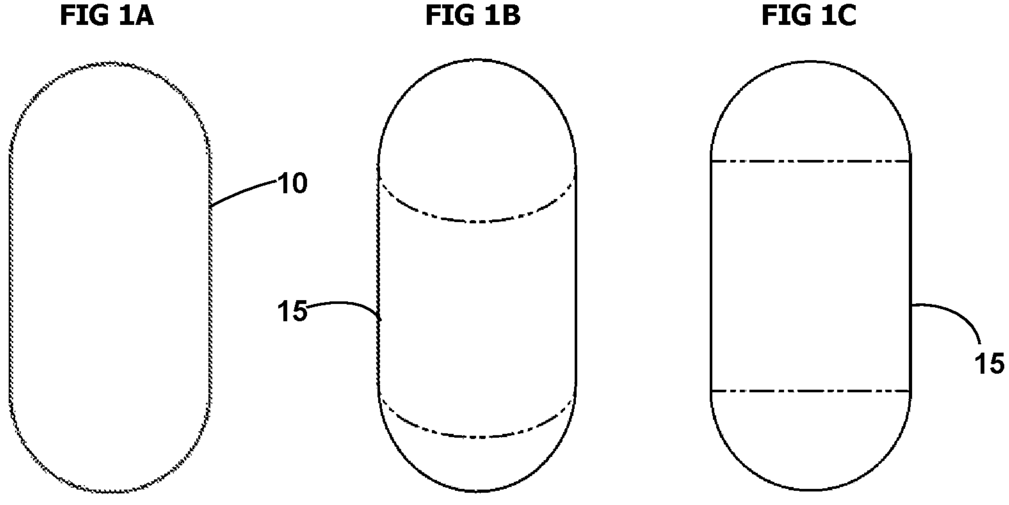
FIG 1A
FIG 1B
FIG 1C
10
15
15
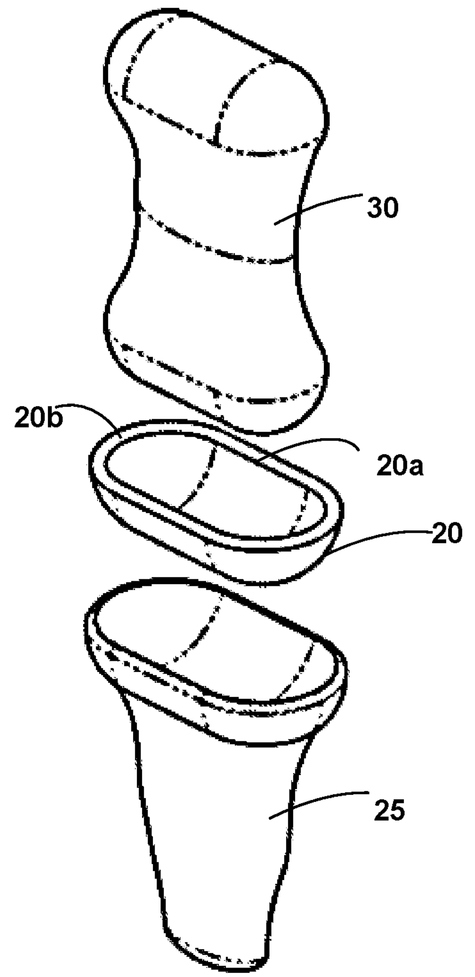
FIG 2
30
20b
20a
20
25

215
217
217
217
SECTION D-D
C
217
217
217
D
D
C
217
210
215
220
210
215
220
210
215
220
210
215
220

IMPLANT

FIELD OF THE INVENTION

The present invention is directed to a hinge joint implant and the insertion of and use of such an implant within a hinge joint. In particular the invention can provide an implant for location within interphalangeal joints such as in proximal and distal interphalangeal joints, for example in fingers and toes. The invention can still further provide an implant for use in treating degenerative joint diseases and disorders such as arthritis and/or torn or damaged cartilage. The present invention also provides for the formation, and also in situ deformation of such an implant.

BACKGROUND TO THE INVENTION

The musculoskeletal system is a complex system involving a combination of the muscular and skeletal systems working together, and it includes bones, joints, ligaments, tendons, muscles, and nerves. Joints in the body are comprised of two or more bones that articulate against each another. There are several types of joints in the body which may be classified according to the amount of mobility permitted and the type of tissue connecting the bones. The amount of mobility permitted by a joint allows classification as a fixed synarthrosis joint, a slightly movable amphiarthrosis joint, or as a freely movable synovial joint. Alternatively, based on the type of tissue that connects the bones, the joint may be classified as a fibrous, cartilaginous, or synovial joint.

A synovial joint, also known as a diarthrosis joint, allows bones to move smoothly and freely against each other in a joint cavity. There are six essential structures of synovial joints which are: pivot, gliding, ball and socket, saddle, condyloid, and hinge joints. A hinge joint, also known as ginglymus, can be found in, for example, a hand, such as in a finger or a thumb, in feet such as in toes, in an elbow, and ankle. A hinge joint comprises a connection between two or more bones whose articulating surfaces may be lined with cartilage, and a joint cavity that is filled with synovial fluid. A synovial membrane lines the interior surface of the joint cavity and secretes synovial fluid. The principal role of the synovial fluid is to reduce friction during the movement of the joint between the bones and/or cartilage. The joint cavity is surrounded by walls of connective tissue in an enveloping articular capsule.

Hinge joints are uniaxial because they contain articular bone surfaces that are moulded to each other in such a way to allow natural movement in a single anatomical plane, either by flexion or extension. Flexion refers to bending and extension refers to straightening of the hinge joint. Thus, the ends of the bones in a hinge joint are suitably shaped to allow motion in the two directions, namely forwards and backwards, with minimal side-to-side motion. This may be achieved by having a concave-shaped bone-end and a complementary convex-shaped bone-end at the hinge joint. The convex shape of the end of one bone surface articulates against the concave surface of another bone. Most hinge joints comprise a pair of condyles, where articulation occurs of a convex-shaped bone-end and a concave-shaped surface of a bone-end, and a central non-articulation area.

The efficient functioning of joints in the human body is extremely important for mobility and quality of life. This is also the case for the hinge joint, and non-functioning of the hinge joint can severely curb the quality of life of a patient. The two main surgical options for a non-functioning hinge joint are bone fusion, also known as arthrodesis, total bone replacement, also called arthroplasty, and bone surface replacement, also known as bone resurfacing. In arthrodesis, the bones of the joint are fused together to create a joint that is stable and essentially pain-free however the fused bones provide little flexibility or movement. Alternatively, arthroplasty involves the surgical reconstruction of a joint by removing the damaged joint and replacing it with an artificial implant with the goal of relieving pain and restoring shape and some function, however the results are generally less than satisfactory at least because the implants do not fully replicate normal joint function.

The treatment of a non-functioning hinge joint with an implant has its disadvantages. Most hinge joint implants are made from silicone rubber, which is flexible but breaks and slips from its position easily. Some studies have found that up to 30% of silicone implants fail within 10 years. Several types of metal hinged implants have also been developed but they all share common problems of bone absorption, implant loosening, and osteophyte formation. There are also other disadvantages to using a metal-based implant such as residual metal is transferred to the bloodstream. Therefore metal hinged implants are used much less often than silicone implants in surface replacement arthroplasty. The surface replacement PYROCARBON implant which acts as a bone-replacement moiety has also frequently been reported to loosen in long-term follow-ups, and histologic examination has shown these implants have poor implant-bone osteointegration in vivo. Additionally, ligaments are often damaged or sacrificed using these implants.

Therefore, whilst implants exist for treating damaged hinge joints, the implants still suffer from various disadvantages and drawbacks. For example, implants can still be difficult to insert into a patient and existing implants do not optimise articulation of the components of the joint and are known to cause discomfort. Additionally, further wear of the joint may still occur in a patient.

There is therefore still a need for an improved hinge joint implant. For example, an implant that is very bone conserving and requires minimum or no reshaping of the bone or cartilage and restores normal joint function.

Small joint arthritis presents a large societal burden throughout Europe. The largest pan-European study on Osteoarthritis (OA) of the hand observed an average incidence of 16.3%. An ageing population is experiencing OA due to increased levels of obesity, and due to people remaining active later in life, imposing long term loading on their joints. The rise of technology has also increased the incidence of finger joint arthritis in young adults as a result of using electronic hand held devices.

It is desirable to maintain independence in older age and later-life and the wellbeing of an individual can be dependent upon many factors including the articulating points of the skeletal system. Surgical processes can be used to improve/maintain joint quality and integrity, particularly for small joints, but success rates for forming artificial joints in this manner are very low (revision rates of up to 40% have been reported for finger prostheses). This is because the implants are invasive, sacrifice large amounts of tissue, and most critically, they do not restore the original kinematics of the joint, leading to pain and discomfort due to unnatural loading of the tissues. As will be appreciated, the present invention seeks to provide for an extremely thin, self-lubricating compliant implant that is placed between the articulating surfaces of the affected joint. Uniquely amongst all implants, motion can occur solely within the device, restoring the natural joint kinematics. Various advantages can arise in so far as it is minimally invasive, does not remove healthy bone, is suitable for patients of all ages, and does not require the use of general anaesthetics. The invention can therefore provide a revolutionary means of treating small joint arthritis and contribute positively to society as a whole by reducing the burden of pain for the great number of current sufferers. Individuals can then be empowered to re-integrate with society with confidence. Small joint reconstruction is predicted to experience the fastest growth globally due to the number of emerging markets and the ageing population and so the advantages of the invention can be widely appreciated.

SUMMARY OF THE INVENTION

According to one aspect of the present invention, there is provided a hinge joint implant for an articulating two-component joint, and arranged when in situ in a joint cavity to comprise at least a substantially hemi-spherocylindrical configuration and which further comprises:

i) a sac formed of deformable material and comprising an outer layer; and ii) a filler inside the sac;

wherein, the filler comprises a material with a coefficient of friction that allows opposite sides of the sac to move relative to one another when a force is applied to the joint, and an outer surface of the sac is arranged not to move relative to the joint component surface it is in contact with, during articulation.

In one aspect, the at least substantially hemispherocylindrical configuration can comprise a radius for articulation.

In a particular aspect of the invention, the implant can comprise a hollow hemispherocylindrical configuration. The implant can comprise such a configuration both prior to, and after, insertion into the joint cavity.

In a further embodiment there can be provided a hinge joint implant configured to fit in a joint cavity wherein the implant extends around the sides of a joint component, for example the sides of a bone and/or cartilage or a bone-replacement moiety. In one aspect, the implant can comprise a substantially spherocylindrical configuration. In one aspect, the implant can have a radius which is sufficient for permitting articulation. In a further aspect, the implant comprises a substantially squashed hemi-spherocylindrical or a substantially squashed spherocylindrical configuration. In another aspect, the implant can be inserted into a hinge joint such as an interphalangeal joint, for example into a distal interphalangeal joint (DIP) and/or a proximal interphalangeal joint (PIP).

The present invention can provide a hinge joint implant for use in the treatment or prophylaxis of a disease or condition in which the hinge joint is indicated, for example in a degenerative joint disease and/or torn or damaged cartilage. The degenerative joint disease comprises arthritis such as OA and rheumatoid arthritis (RA). OA degrades the cartilage that protects the ends of the bones.

The present invention can also provide a method of treatment or prophylaxis of a disease or condition in which the hinge joint is indicated in a patient in need thereof, comprising administering the implant described herein, for example which is therapeutically effective.

The present invention can further provide the use of any hinge joint implant described herein for inserting into a hinge joint.

Since the implant can offer a low trauma approach to addressing joint pain, it is not only suitable for insertion where the patient has severe joint deterioration but may also offer advantages when inserted at an early stage. For example, where tests such as scans or xrays indicate that deterioration of the bone and/or cartilage has started, the implant of the present invention may be utilised such that further damage is reduced and preferably prevented such that implantation of a full prosthesis is deferred or even avoided. Similarly the implant of the present invention may be implanted at a very early stage such as when a blood test or other assay shows markers for arthritis.

Further, the present invention can also provide a method of forming a hinge joint implant described herein, which method can include forming the implant from one or more members, for example manufacturing the implant from two or more pieces that are optionally subsequently welded together.

In one embodiment, the implant can be configured to fit entirely within the joint cavity. For example, the implant need not extend over the ends of the joint components, such as bone and/or cartilage or a bone-replacement moiety. Further, ligaments in the joint cavity are not compromised.

Still further, in one embodiment, the implant of the invention can be configured to extend beyond the joint cavity. In one aspect, the implant extends around the sides of the joint component, for example bone and/or cartilage in the joint or a bone-replacement moiety. For example, the implant can extend around an end of the joint component, for example around bone and/or cartilage in the joint or around a bone-replacement moiety. Thus, the implant can be configured to extend beyond the joint cavity, and may have a greater transverse diameter across the joint and the maximum diameter of any vertical cross-section of the implant may be less than the diameter of the equatorial plane of the convex-end of a component of the joint, when compared to an implant that fits entirely within the joint cavity. This allows a wider range of movement as the joint component can move further while remaining in contact with the implant. This may also reduce manufacturing costs, as less sac and filler material may be required. In one aspect, the implant extends to cover a proportion of the joint component, for example bone and/or cartilage or a bone-replacement moiety. For example, the implant can extend to cover a proportion which is just sufficient to secure the implant in position. The interaction of the implant with retained ligaments may be sufficient to hold the implant in position. Thus, no ligament is damaged and the ligaments remain fully functional. The ligaments work with the implant to provide original healthy joint kinematics. Thus the optimum stability of the joint is retained. This is a significant advantage as the implant is loaded in place of original cartilage. The implant may generally be held in position in the joint according to its shape or configuration, and/or according to specifically formed features of configuration. The kinematics of the implant are anatomically-controlled by the shape and position of the implant and undamaged ligament structure.

The implant of the present invention can be of any suitable size and configuration. The selection of the size and configuration of the implant will generally depend on the hinge joint into which the implant is inserted.

As noted, the implant can have an at least substantially hemi-spherocylindrical configuration. In one aspect, the implant can have an at least substantially hollow hemi-spherocylindrical configuration. In an alternative embodiment, the implant has a spherocylindrical configuration. This can have a particular advantage in that the hinge joint implant does not crease during articulation of the joint. The hinge joint implant of the present invention can comprise a hemi-spherocylinder or spherocylinder shape exhibiting a caterpillar-track type motion within the hinge joint during articulation.

In a further aspect, the configuration can be arranged to be deformed so as to be at least slightly flattened or squashed once inserted for articulation in the joint. In a yet further aspect, the implant is arranged to present a concave portion during articulation. The concave portion allows the implant to fit around the end of the joint component surface, for example the surface of bone and/or cartilage or a bone-replacement moiety at the joint. For example, the concave portion of the implant can fit around a convex-shaped end of the joint component, such as bone and/or cartilage or bone-replacement moiety in the joint.

In one embodiment, the implant can comprise a filler-filled implant of substantially capsule-like arrangement which may be deformed when located in the joint cavity for articulated movement of the joint components, which are for example bones with/without cartilage or bone-replacement moieties. In one aspect, the implant can comprise a plurality of, and for example a pair of, filler-filled implants. Each of the filler-filled implants can be arranged such that they can be deformed by respective condyles of the joint components. In a further aspect, the filler-filled implant can be arranged to be deformed from a substantially capsule-like configuration to a non-capsule like configuration. In one aspect, the filler-filled implant can comprise a gel-filled capsule.

Such an implant of a capsule-like configuration can be arranged to adopt or maintain a substantially squashed spherocylindrical configuration as it is compressed between the joint components. Also, such an implant can be arranged to be deformed into, or from, a substantially hemi-spherocylindrical configuration during location between the joint components.

A hemi-spherocylindrical configuration has a number of potential positive implications on the method of manufacture of the implant, for example when using rapid prototyping. In one embodiment, the implant can be manufactured from two pieces of quarter spherocylinders which are subsequently welded together.

In one embodiment, the implant comprises a sac formed of flexible material with a filler or a surface treatment inside the sac that will impart a very low coefficient of friction thus enabling the opposite sides of the sac to move relative to one another when a force is applied to the joint.

In another embodiment, the sac can comprise a polymer. In one aspect, the polymer can comprise, or is, a natural or a synthetic polymer. Examples of suitable polymers include polyhydroxyalkanoates, polycarbonate urethanes, polyurethane, urethane, silicones, polycarbonate urethane based silicones, and those based on cellulose. Polyurethane has excellent flexural fatigue strength and biocompatibility. In one aspect, the sac is comprised of biocompatible elastomeric polymer. In a further aspect, the sac can comprise polyurethane. In one aspect, the sac can comprise polycarbonate urethanes, urethane, or polycarbonate urethane based silicones. In one aspect, the sac is not made of metal.

In another embodiment, the filler material inside the sac may be any material that has the coefficient of friction required to allow opposite sides of the sac to move relative to one another when a force is applied. In particular, the implant prevents sliding movement at the joint surfaces, which reduces friction and pain and therefore works to prevent further damage of the bone and/or cartilage. In addition, the structure of the implant of the present invention may provide some cushioning between the bones which make up the joint. In one aspect, the amount of filler will just be sufficient to allow the relative movement within the sac. Thus, opposing sides of the sac may be touching and the filler simply provides lubrication between the sides. In one aspect, the sac contains a lubricious fluid or gel in combination with possible internal coatings which provide the self-lubricating function. The internal surface of the implant may be treated with a surface coating to aid lubrication and reduce wear. Throughout, biocompatible materials are used. In another aspect, the implant can comprise filler material which is a fluid or gel. In yet another aspect, the filler material can comprise a gel. In a further aspect, the amount of fluid or gel in the filler is just sufficient for the implant to be only slightly squashed in the joint cavity. Examples of suitable filler materials include a phospholipid or an elastomer. In one example the filler material may be a hyaluronic acid based hydrogel, a natural polymer or an alginate-based hydrogel. A caterpillar-type action within the implant can provide for the improved articulation of the joint.

In one embodiment, the implant does not move relative to the joint-component surface due to the coefficient of friction during articulation. For example, the coefficient of friction is the result of inter-surface contact between the surfaces of the sac and the joint component. In a further aspect, the implant does not move relative to the joint-component surface due to an adhesive or mechanical fixture. Thus, the implant is adhered to the joint component surface by using additional means in a selective area that will not interfere with the required range of motion. In a further aspect, the sac can include an adhesive or mechanical fixture. In a yet further aspect, the outer surface of the sac when in use can contact the joint component surface, for example the joint component is a bone and/or cartilage or a bone-replacement moiety of the hinge joint, and which has a coefficient of friction such that it does not move relative to the joint component surface, for example bone and/or cartilage or a bone-replacement moiety, with which it is in contact during articulation. In an additional aspect, the filler can allow opposite sides of the sac to move relative to one another when a force is applied. In an alternative aspect, the outer surface of the sac comprises an adhesive or mechanical fixture.

As a particular advantage, the said at least hemi-spherocylindrical configuration can exhibit a caterpillar-track type motion during articulation but without any creasing of sac material inhibiting the smooth motion of articulation. In one aspect, the filler material is a fluid or gel. A further advantage if the present invention can be that the presence of the implant does not perturb the anatomical loading through the hinge joint. Since the implant of the present invention does not involve articulating metal parts, small particles such as metal ions are not released as a result of the movement. In a further aspect, the sac material is an elastomeric polymer and the implant has a hemi-spherocylindrical configuration such that the implant exhibits a caterpillar-track type motion when squashed and/or compressed and without any creasing. Generally, the sac material will have sufficient strength to withstand implantation and articulation of the hinge joint, while being sufficiently flexible such that the implant can mould to sit against the bone and/or cartilage once it is in position without preventing articulation.

The dimensions of the implant will depend upon the hinge joint into which the implant is inserted. For example, the implant for a finger will generally have smaller dimensions than the implant for an elbow. In one embodiment, the implant may be between about 4 mm to about 25 mm in length and/or width. In one aspect, the implant is about 20 mm in length and/or width. In one aspect, the implant may be between about 2 mm to about 20 mm in length and/or width. In one aspect, the implant is about 10 mm in length and/or width. For example, the shape or configuration of the implant is at least hemi-spherocylindrical, or substantially squashed spherocylindrical, and the implant is about 2 mm to about 20 mm in length and/or width. In an alternative aspect, the implant is greater than 20 mm in length and/or width.

The thickness of the implant can be the thickness across the sac and the filler. In one embodiment, the thickness of the implant would be approximately equal to the same order of magnitude as the reduction in cartilage thickness. In one embodiment, the implant comprises a thickness of from about 0.01 mm to about 1.0 mm or about 1.5 mm for small joints. In one aspect, the thickness is of up to 1 mm. In a further aspect, the thickness is 0.25 mm. The thickness may be uniform or non-uniform throughout the implant. In one aspect, the implant may have a consistent thickness throughout its size and in another aspect, it may vary in thickness. The implant may be thinner in a central region in one aspect, and suitably in an alternative aspect it may be thicker in the central region. In another aspect, the thickness comprises from about 0.05 mm to about 0.8 mm and may be useful. In another aspect, the thickness comprises from about 0.2 mm to about 0.5 mm and may also be useful. The length and width of the implant will depend on its eventual use and the implant will generally have a thickness of about 0.05 mm to about 0.8 mm. In a further aspect, the thickness is about 0.1 mm, 0.2 mm, 0.3 mm, 0.4 mm, 0.5 mm, 0.6 mm, or about 0.7 mm.

In another embodiment, the implant can comprise regions of different thickness, such as for example a dual thickness configuration. In one aspect, the implant can comprises a localised thickening in the load bearing area. For example, the implant can comprise a load bearing thicker surface which allows for the caterpillar motion at the extremities of the implant to have a larger radius and reduces the induced stress in this area as well as acting as a lubricant reservoir. Another potential advantage with the dual thickness concept can be that it increases the flexibility of the manufacturing processes as there are areas that will not be subject to articulation, loading, or high flexion at the extremities. These areas could be exploited for fabrication to employ more conventional manufacturing or fabrication technologies such as ultrasonic welding.

In a further aspect, the sac material thickness will be between 50 and 500 microns and preferably between 100 and 300 microns, to aid compatibility with the available joint space and the thickened section of the implant being approximately twice as thick.

In one embodiment, the outer surface of the sac can be in contact with the joint cavity and/or joint component. In one aspect, the outer sac surface can be comprised of uniform material. In one aspect, the surface of the implant may be smooth such that it is the coefficient of friction of the sac material alone which provides the friction to prevent the implant from moving with respect to the joint replacement surface, for example with respect to bone and/or cartilage or a bone-replacement moiety. In another aspect, a coating may be provided on the outer surface of the sac to increase the friction.

In one embodiment, the outer surface of the sac may be roughened in at least some regions to increase the friction between the implant and the joint component surface which may be for example bone and/or cartilage or a bone-replacement moiety. For example, the sac could be coated with a material to encourage bone adhesion and to act like an adhesive. In one aspect, the outer surface of the sac may be formed from a material which wrinkles as the joint articulates and these wrinkles provide the coefficient of friction required to prevent the implant from moving with respect to the joint component, for example bone and/or cartilage or a bone-replacement moiety. In one aspect, the implant of the invention is simple to construct and relatively low-cost to manufacture.

In one embodiment, the outer surface of the sac can be coated with a coating material to facilitate bone and/or cartilage repair. In one aspect, the filler material facilitates bone and/or cartilage repair.

In one embodiment, the coating material may be pharmaceutically active material and/or the pharmaceutically active material may be located in the filler material in which case the material from which the sac is formed will allow release, preferably slow release, of the pharmaceutical material. Suitable pharmaceutical materials include those for pain relief or which are anti-bacterial. In one aspect, the outer surface of the sac may be coated with a pharmaceutical material, which provides appropriate pain relief immediately after an operation, and a second pharmaceutical material, which provides pain relief over time, may also be provided in the coating or alternatively within the filler of the implant. In another aspect, the pain relief pharmaceutical material may be chosen such that the quantity delivered over time reduces. The pharmaceutically active material could offer more advantages for younger patients. It may be advantageous for cartilage repair for example in sports injuries where the implant could be later removed. The pharmaceutically active material may be used to accelerate healing, with, for example, stem cells.

It may be desirable to utilise adhesive, for example, a small amount of adhesive at the time of implantation. In one embodiment, the part of the implant that stays in contact with the joint component which is bone and/or cartilage contains the adhesive. In one embodiment, the outer sac surface can comprise an adhesive and/or mechanical fixture. In one aspect, the outer sac surface can comprise an adhesive and/or mechanical fixture. For example, the adhesive can be placed in the centre of the outer surface of the sac. In one aspect, the adhesive may merely comprise a spot of a suitable biocompatible adhesive. In one aspect, the adhesive can comprise any suitable biocompatible adhesive. In a further aspect, the biocompatible adhesive can comprise a glue. In an alternative aspect, the mechanical fixture can comprise any suitable mechanical fixture such as a protruding plug on the implant that fits in a small hole in the bone. In another aspect, the implant can be fixed from the centre point of the hemi-spherocylinder to the intact ligaments, for example the fixture runs through the implant. In an alternative aspect, the fixtures can be arranged to attach each end of the implant to the ligaments intact, for example the fixture would still remain central after quashing the in situ implant. In one aspect, the adhesive can delivered to the implant by way of a bore provided through the joint component and opening beneath the surface of the in situ implant. A localised anchor position adhesive or mechanical fixture can be provided to act to supplement friction.

In one embodiment, the implant can be positioned between the joint components such that the components are aligned correctly relative to each other. Failure to achieve this accurate alignment may result in the patient experiencing discomfort which may be due to inappropriate frictional forces and wear. Such forces can damage the components and reduce mobility.

In one particular aspect, a patient may have a preoperative scan and the shape and size of the joint can be measured. Based on this information, the implant can be manufactured to be the optimum configuration for the patient. Thus, in one aspect, a patient-specific implant may be produced.

A further advantage of the implant of the present invention is that it may be readily introduced without the need for major invasive surgery. The surgery required to insert the implant of the present invention will generally be minimally invasive. In one embodiment, the implant may be configured such that it can be delivered arthroscopically. In one aspect, such as where the implant is to be inserted into a hinge joint, incisions which are only from about 5 mm in length may be sufficient. It will therefore be understood that arthroscopic introduction provides substantially less trauma to a patient then implantation of a conventional prosthesis or of a revision operation. Additionally, the chance of infection is reduced. In the majority of circumstances, a general anaesthetic will not be required and insertion may be carried out under local anaesthetic. Being able to avoid the use of a general anaesthetic is desirable with frail, elderly patients who often have pre-existing medical conditions which exacerbate the risk of adverse effects of the anaesthesia and surgical procedure. Therefore, a permanent implant such as that of the present invention is likely to offer advantages for elderly patients.

It will however be understood that the implant of the present invention is suitable for implantation in any patient. For patients, the minimal invasive nature of the surgery required is beneficial as the required recovery time and risk of complications is significantly reduced when compared with conventional prosthesis implantation. Since the implant can be readily implanted without the need for substantial surgery, the implant may be used to provide temporary relief or to defer the need for revision surgery.

In one embodiment, the implant can be provided for inserting into a hinge joint in a hand, foot, ankle, or elbow. There are currently no or relatively poor surgical options of implants for use in hinge small joints in the fingers and toes. In one embodiment, the implant can be arranged for inserting into a hinge joint in a hand or foot. In one aspect, the implant can be provided for inserting into a hinge joint in a thumb, finger, or toe. In another aspect, the implant can be arranged for inserting into a hinge joint in a finger. In one aspect, the joint component is bone and/or cartilage that the implant extends around, for example the joint component is a phalanx. In another aspect, the bone is a distal, middle, or a proximal phalanx.

Whether arthrodesis or arthroplasty is used generally depends on the joint needing repair. In one embodiment, the implant is useful in small hinge joints such as in the two interphalangeal joints of fingers, namely the PIP and DIP joints, in the thumb, but also in the toes, elbow, and ankle. In one aspect, the hinge joint is an interphalangeal joint. In a further aspect, the interphalangeal joint is a distal interphalangeal (DIP) joint and/or a proximal interphalangeal (PIP) joint.

In one embodiment, the implant of the invention can be for use in therapy. Arthritis affects the joints and typically results in pain and stiffness of the affected joint, which can severely curb the quality of life of a patient. Thus, in one aspect, the implant is for use in treating arthritis, and/or torn or damaged cartilage. In one aspect, there is provided use of the implant for treating arthritis, and/or torn or damaged cartilage.

In a further aspect, there is provided the use of a hinge joint implant for inserting into a hinge joint. For example, an interphalangeal joint such as a DIP and/or a PIP joint.

In a yet further aspect, there is provided a method of treatment or prophylaxis of a disease or condition in which the hinge joint is indicated in a patient in need thereof, comprising administering the implant described herein. For example, administering a therapeutically effective implant to a human in need thereof.

The invention can therefore provide for a hinge joint implant configured to fit in a joint cavity for use in the treatment or prophylaxis of a degenerative joint disease, and/or torn or damaged cartilage. For example, the degenerative joint disease comprises arthritis, including OA and rheumatoid arthritis (RA).

About half of all women and one-quarter of all men will experience the stiffness and pain of hand OA by the time they are 85 years old. OA causes the smooth, protective cartilage on the ends of your bones to break down and wear away. Over time bones rub together, causing pain. Along with cartilage loss, OA also causes bone spurs to form. Bone spurs in and around the joints increase joint stiffness and pain. With worsening OA, daily activities can become difficult and finger joints may lose their normal shape. DIP and PIP joints are prone to stiffness and a significant loss of motion, usually as a result of OA.

Replacement surgery is sometimes used to relieve these symptoms, especially in the middle and ring fingers, which need to remain flexible for gripping. But these joints get heavy use, so implants can wear out quickly. One problem is that hinged finger implants do not fully replicate normal finger motion.

Arthrodesis is commonly used to treat arthritis pain in the DIP as there are few to no reliable implants for this joint. It usually results in a stable, pain-free and reasonably functional joint. However, the most serious complication is failure of the resulting fused bones to grow together or properly align, which may require further surgery. Motion is one of the biggest failings of finger surgery. Not only does it not improve after treatment, it is often reduced further in the pursuit of pain relief.

In one embodiment, there is provided a method of locating an implant within a hinge joint cavity comprising manipulating the joint components and associated ligaments and subsequently allowing the joint components to compress, for example squash, the implant for articulated movement of the joint. For example, the implant during location, and after subsequent compression, maintains at least a substantially hemi-spherocylindrical configuration. In a further aspect, the implant comprises a hollow concave centre opening. In an alternative aspect, the implant can comprise a filler-filled capsule maintaining substantially a capsule configuration during location and after subsequent compression.

In another embodiment, the implant may further comprise a spacer, which may be suitably shaped and sized to align the bones as required or prevent the first component of the articulating joint from contacting the other components of the articulating joint. In one aspect, the spacer can be arranged to engage a component of the articulating joint and the implant. If the implant has a hollow concave side, it may be the concave side of the implant that engages the spacer. Thus, in one aspect, the spacer may engage with the sac of the implant. This will position a component of the articulating joint away from the other components of the articulating joint such that they do not come into contact with each other during movement of the joint. Further, the spacer may be integral to the sac. This improves the ease of manufacture and insertion. In another embodiment, the spacer may be enclosed within a membrane in the implant.

The spacer need not be part of the implant. Therefore, an alternative aspect provides a kit of parts, including the implant and a spacer, and optionally instructions for use thereof. This allows a suitable spacer for the specific joint to be selected. Whilst the implant of the present invention will generally be used with natural bone, it may offer some advantages when used with a prosthesis. For example, the implant may be used to provide relief when a previously implanted prosthesis is exhibiting wear.

The hinge joint implant can be formed such that it can be inserted using a minimally invasive method, by preserving the tissue, and retaining natural joint kinematics and/or loading. There is no external wear mechanism and the caterpillar movement is contained within the implant such that there is no movement between the external surface of the implant and the bone and/or cartilage surface. In one embodiment, there is provided a method for manufacturing a hinge joint implant from one or more pieces. Standard methods to produce three-dimensional geometries are well known in the art, for example rapid layer manufacture (also known as rapid prototyping). Rapid prototyping involves an additive procedure that allows three-dimensional geometries to be created layer by layer using a polymer. Such methods may be used to manufacture the implant from two or more pieces. For example, in one aspect the implant is manufactured from two or more pieces that are optionally subsequently welded together or rapid prototyped from an elastomeric polymer.

In one embodiment, the filler material is located within the sac during manufacture and the sac is sealed. There is therefore no requirement for the implant to be filled during implantation. Thus the risk of spillage or leakage of the filler material when filling the implant is obviated. Further, the controlled filling of the implant at the time of manufacture ensures that the implant is filled with the correct amount of filler and that the sterility of the material is maintained.

In one embodiment, the implant comprises two or more separate pieces. In one aspect, the implant can comprise a double-implant comprising two separate pieces. In another aspect, the implant can comprise a triple or quadruple-implant comprising three or four separate pieces. In one aspect, the pieces can be identical. In another aspect, the pieces can be provided adjacent to each other. In a further aspect, the two or more separate pieces may be affixed or anchored by, for example, an adhesive or mechanical fixture to the joint component, for example bone and/or cartilage or a bone-replacement moiety. In another aspect, there may be a gap or gaps present between the separate pieces, which may assist in, for example, the movement in the joint.

In one embodiment, there is provided a hinge joint implant system comprising at least two separate pieces of hemi-spherocylindrical or squashed spherocylindrical configuration.

The implant of the present invention offers the following advantages which sets it aside from current technology. It is bone conservative and very little or no healthy bone needs to be removed. Further, substantially all, if not all, of the joint ligaments can be preserved, and there is no motion between the implant and the joint component surface, for example bone/cartilage/bone-replacement surface, and all motion occurs in the implant acting like a caterpillar track. Unlike all other articulating implants any wear debris is contained within the sac where motion is occurring. The implant fits into the space left as a result of cartilage wear/damage, and anatomical biomechanics are restored. The implant is workable and thin and insertion of the implant is easy to carry out, as is revision implantation because no bone or soft tissue is removed. The implant is more suitable for local anesthetic, and very low friction can be engineered inside the implant. The implant also does not apply any force to the joint unlike the current gold standard one piece silicone implants.

In all aspects of the implant described herein, the implant can have a substantially hemi-spherocylindrical, hemi-spherical, hemi-prolate spheroid, or spherical cap configuration depending on the patient's joint geometry.

As mentioned, the outer surface of the sac can be designed not to move relative to the joint surface it is in contact with during articulation. This could be achieved by the non-compromised natural joint ligament structures and soft tissue restraints, or the external geometry and surface roughness of the implant. In an additional embodiment, there is incorporated a skirt on the implant which could be patient-specific and help hold the implant in position.

All angles of flexion are possible during joint articulation with the implant of the present invention described herein. For example 0 and 70° angles of flexion can be achieved when the implant is situated between the two joint components. In one aspect, the angle of flexion is half the joint articulation angle.

It is to be understood that the terminology used herein is for the purpose of describing embodiments only, and is not intended to be limiting. Unless defined otherwise, all technical and scientific terms used herein have the same meaning as commonly understood by one of ordinary skill in the art to which the invention pertains.

As used in this specification and the claims, the singular forms "a", "an", and "the" include plural referents unless the content clearly dictates otherwise. Thus, for example, reference to "a hinge joint" includes a combination of two or more hinge joints, and the like.

The word "comprise", and variations such as "comprises" and "comprising", will be understood to imply the inclusion of a stated integer or step or group of integers but not to the exclusion of any other integer or step or group of integers or steps. Thus, the term "comprising" encompasses "including" or "consisting" e.g. a process "comprising" X may consist exclusively of X or may include something additional e.g. X+Y. The term "consisting essentially of" limits the scope of the feature to the specified materials or steps and those that do not materially affect the basic characteristic(s) of the claimed feature. The term "consisting of" excludes the presence of any additional component(s).

"About" as used herein when referring to a measurable value such as an amount, a temporal duration, and the like, encompasses a suitable margin of error such as variations of ±50% or ±40% or ±30% or ±20% or ±10%, including ±5%, ±1%, and ±0.1% from the specified value, as appropriate to perform the disclosed methods.

A "cavity" refers to a space. For example, a joint cavity may refer to a space between two or more joint components, for example bone and/or cartilage or bone-replacement moieties, located at a joint.

The term "configuration" describes the spatial arrangement of the constituent parts or elements, for example the spatial arrangement of the implant in a joint cavity. For example, the configuration includes the shape of the implant.

The term "moiety" is used herein to describe an alternative implant that replaces, for example, both joint components in a two-component joint.

"Polyhydroxyalkanoates" (PHAs) are those commonly used in the art such as polyesters that can be either straight chained or branched, including for example poly-(R)-3-hydroxybutyrate (P3HB). PHAs can be either thermoplastics or elastomers, and their mechanical properties can be changed by modification with other polymers, enzymes, and inorganic materials.

"Polyurethanes" are also those used commonly used in the art such as polymers with monomers that are joined by carbamate groups. Any suitable polyurethanes may be used in the present invention. "Polycarbonate urethanes" are also those commonly used in the art and which have carbonate groups, Any suitable polycarbonate urethanes may be used in the present invention.

The term "spherocylindrical" refers to a three-dimensional geometrical shape consisting of a cylinder with hemispherical ends, for example a capsule.

The term "therapeutically effective" refers to the amount of implant that when administered is sufficient to prevent development of, or alleviate to some extent, one or more of the symptoms of the disorder being treated.

Figure 4:
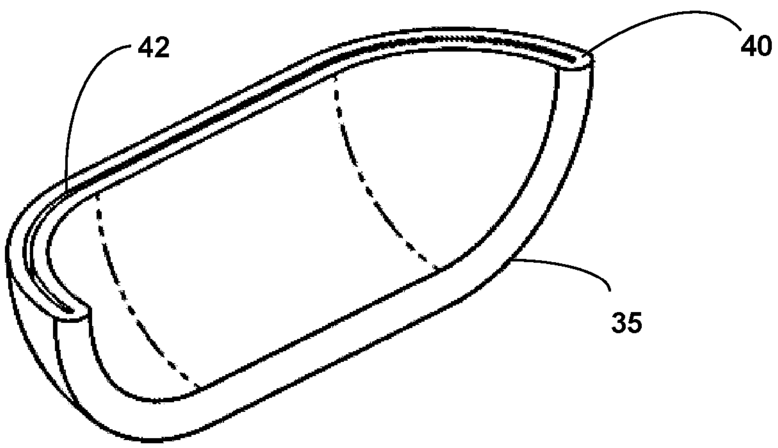
Figure 5A:
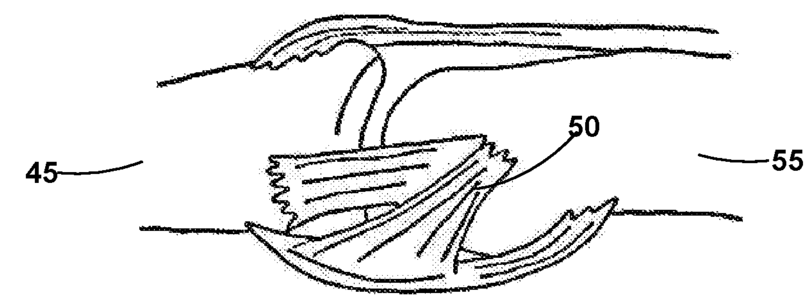
Figure 5B:
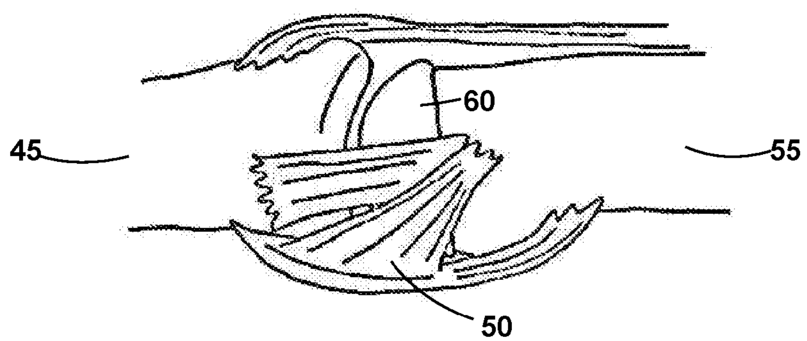
Figure 6:
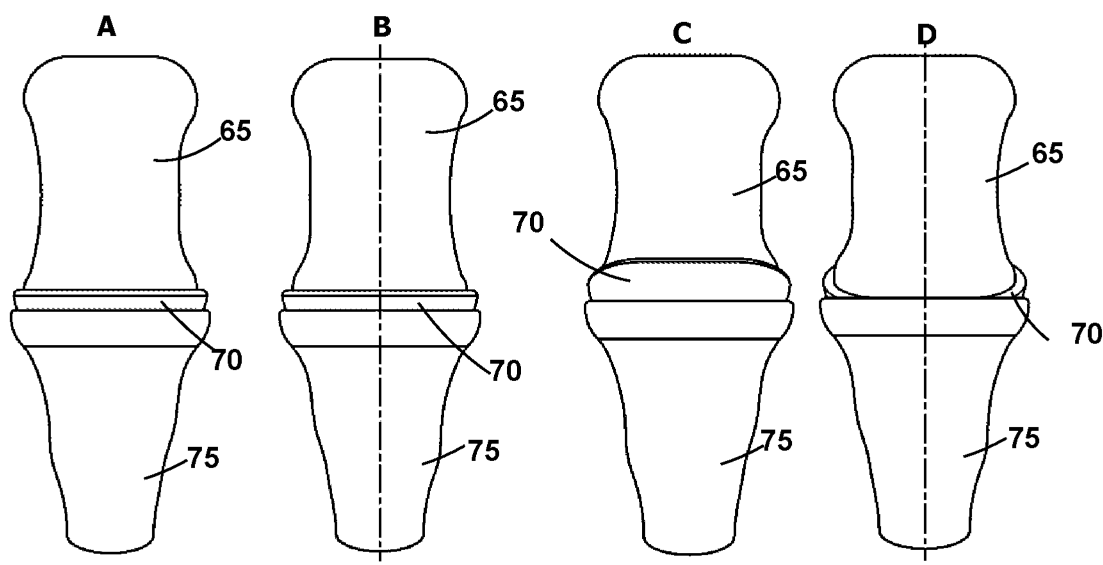
Figure 6:
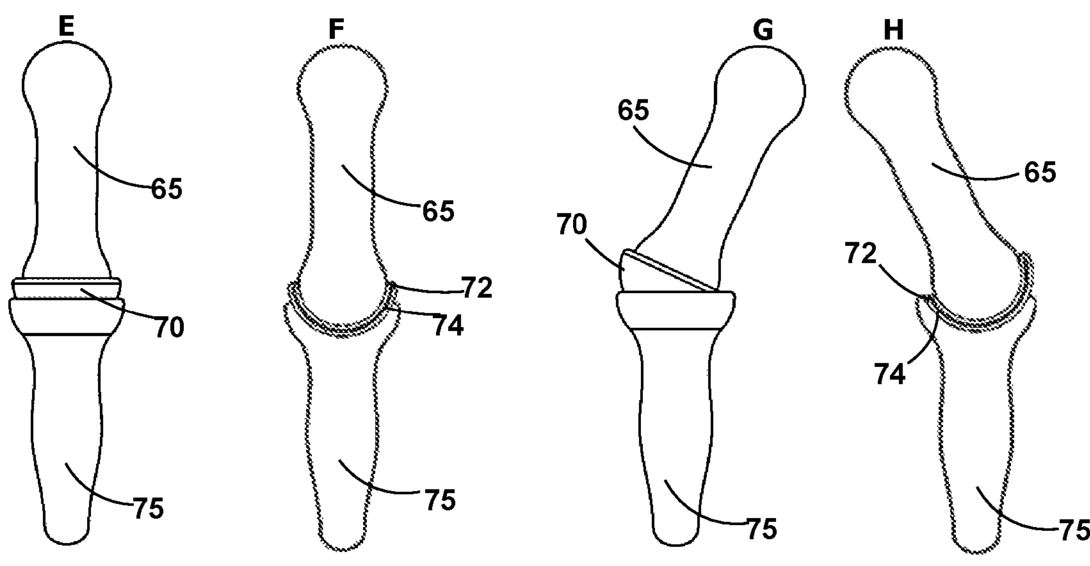
Figure 7:
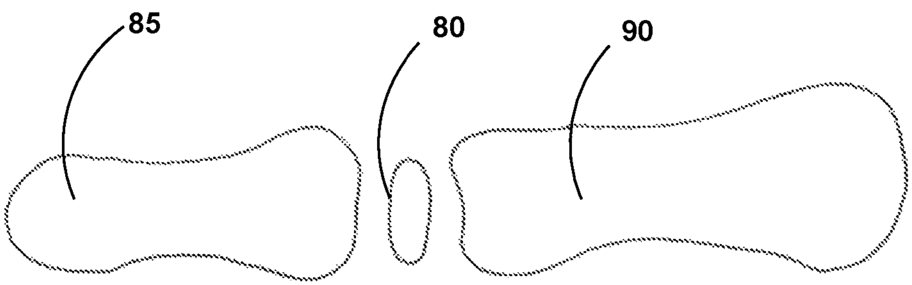
Figure 8:
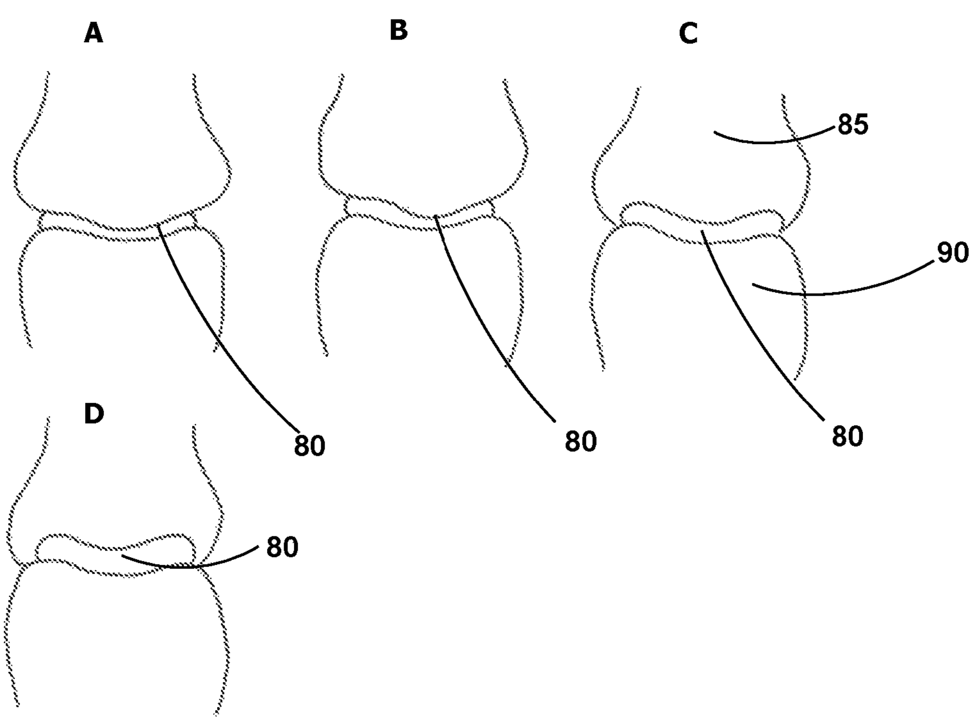
Figure 9:
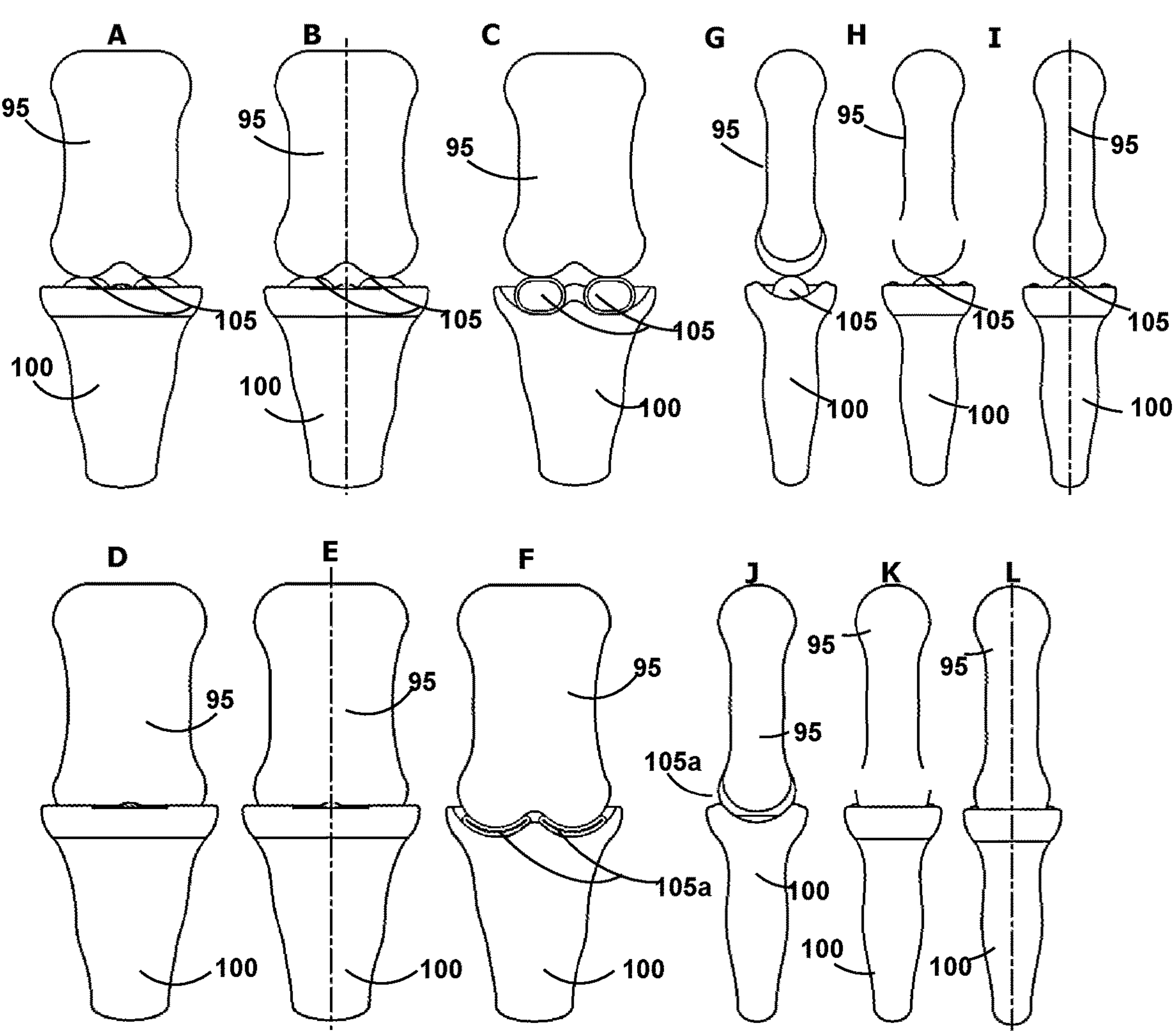
Figure 10:
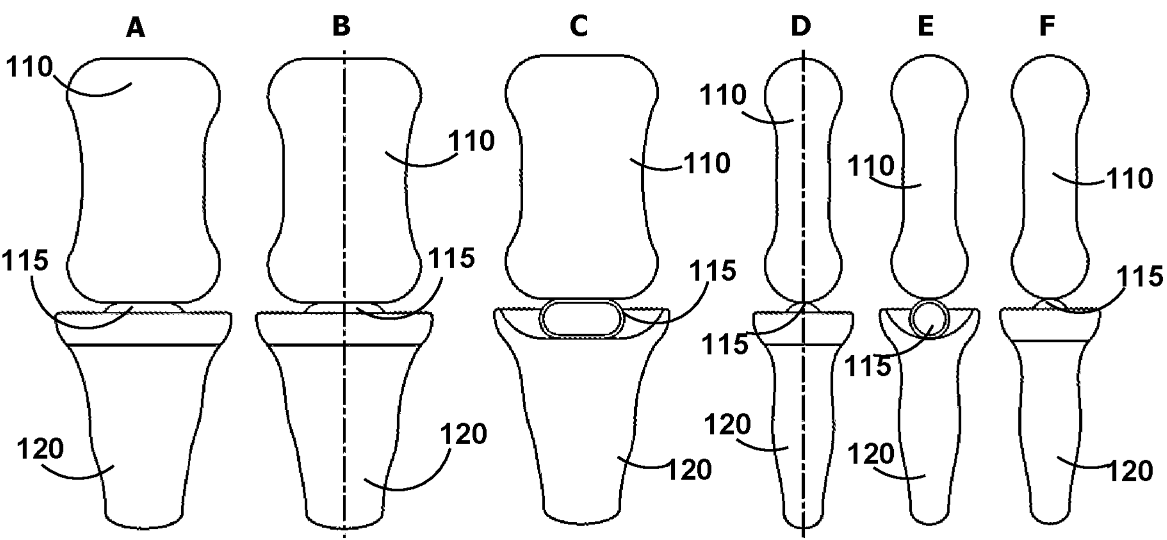
Figure 11:
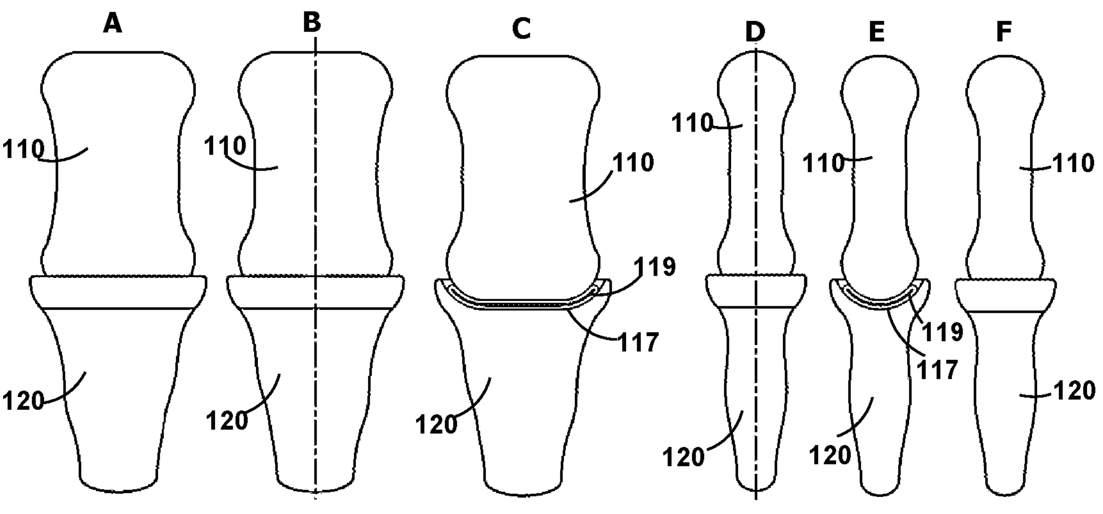
Figure 12:
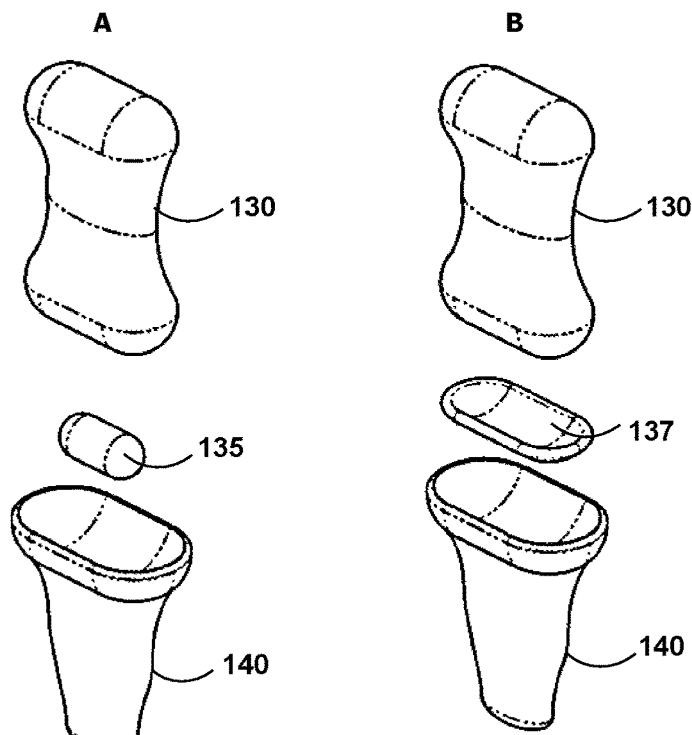
Figure 13:
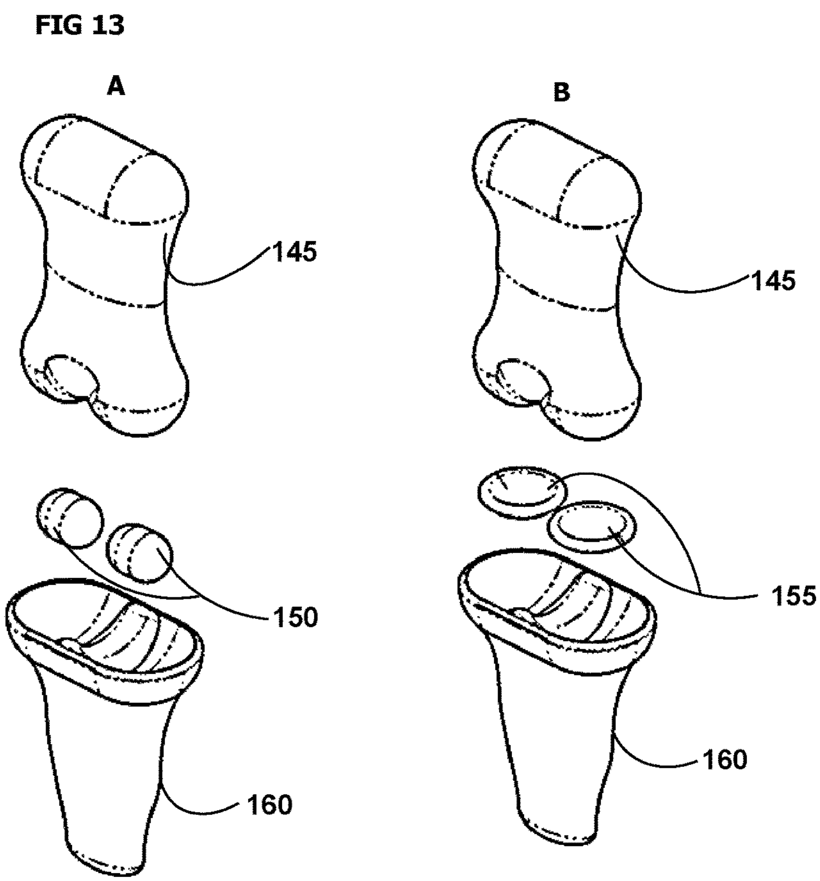
Figure 14:
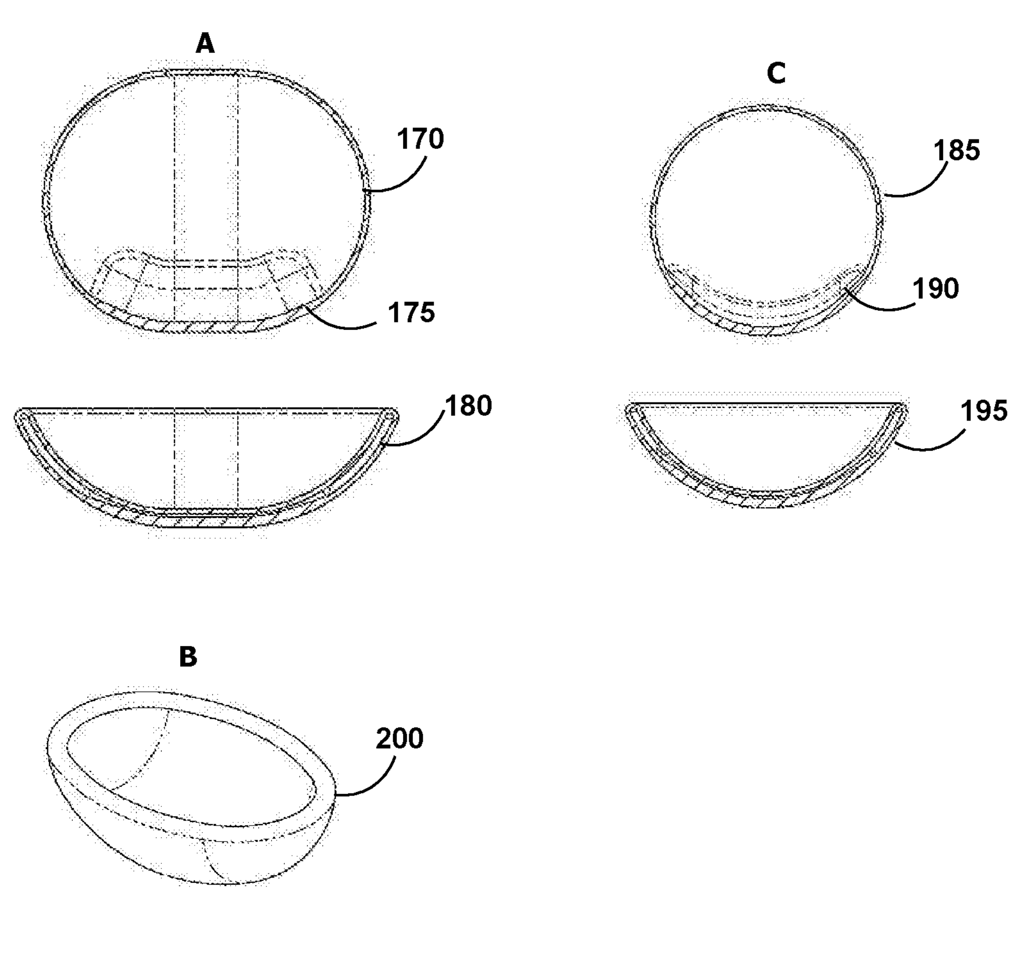
Figure 14:
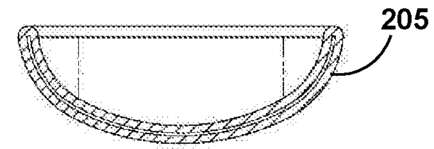
Figure 15:
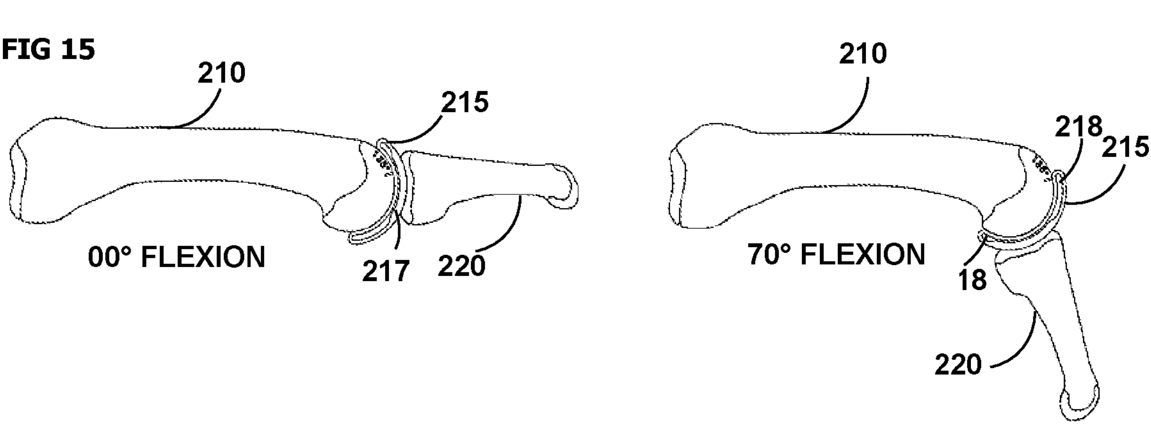
Figure 16:
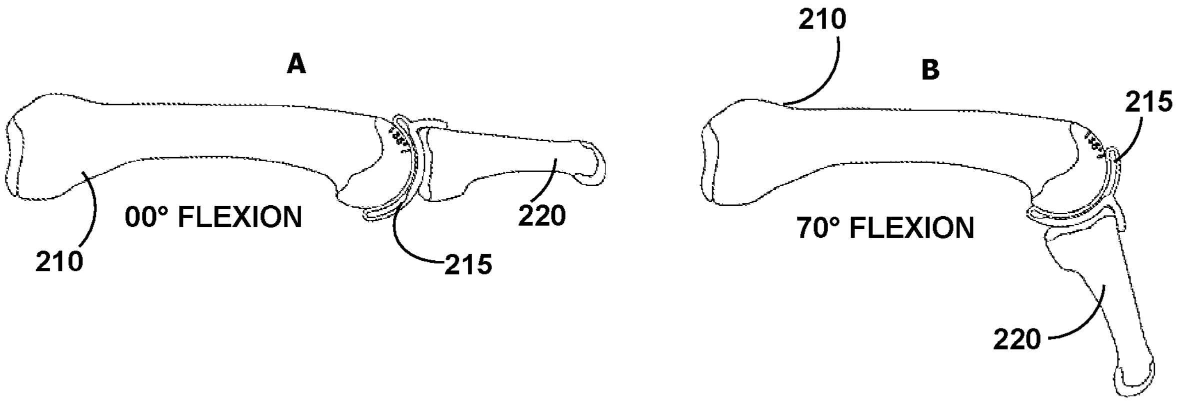
Figure 16:
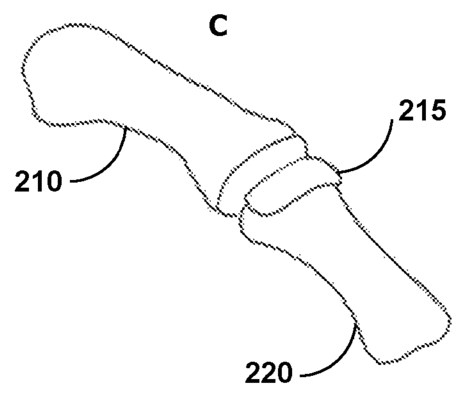
Figure 16:
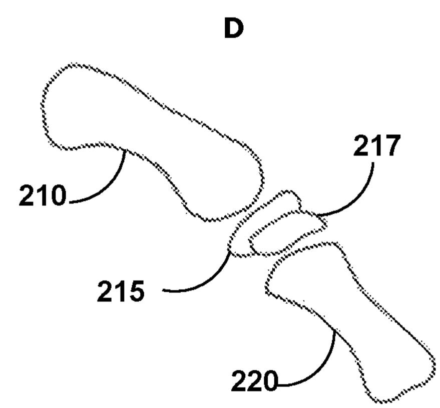
Figure 17:
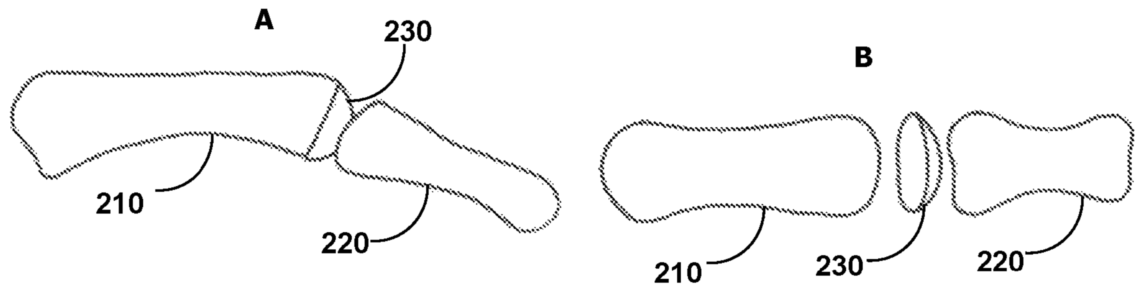
Figure 18:
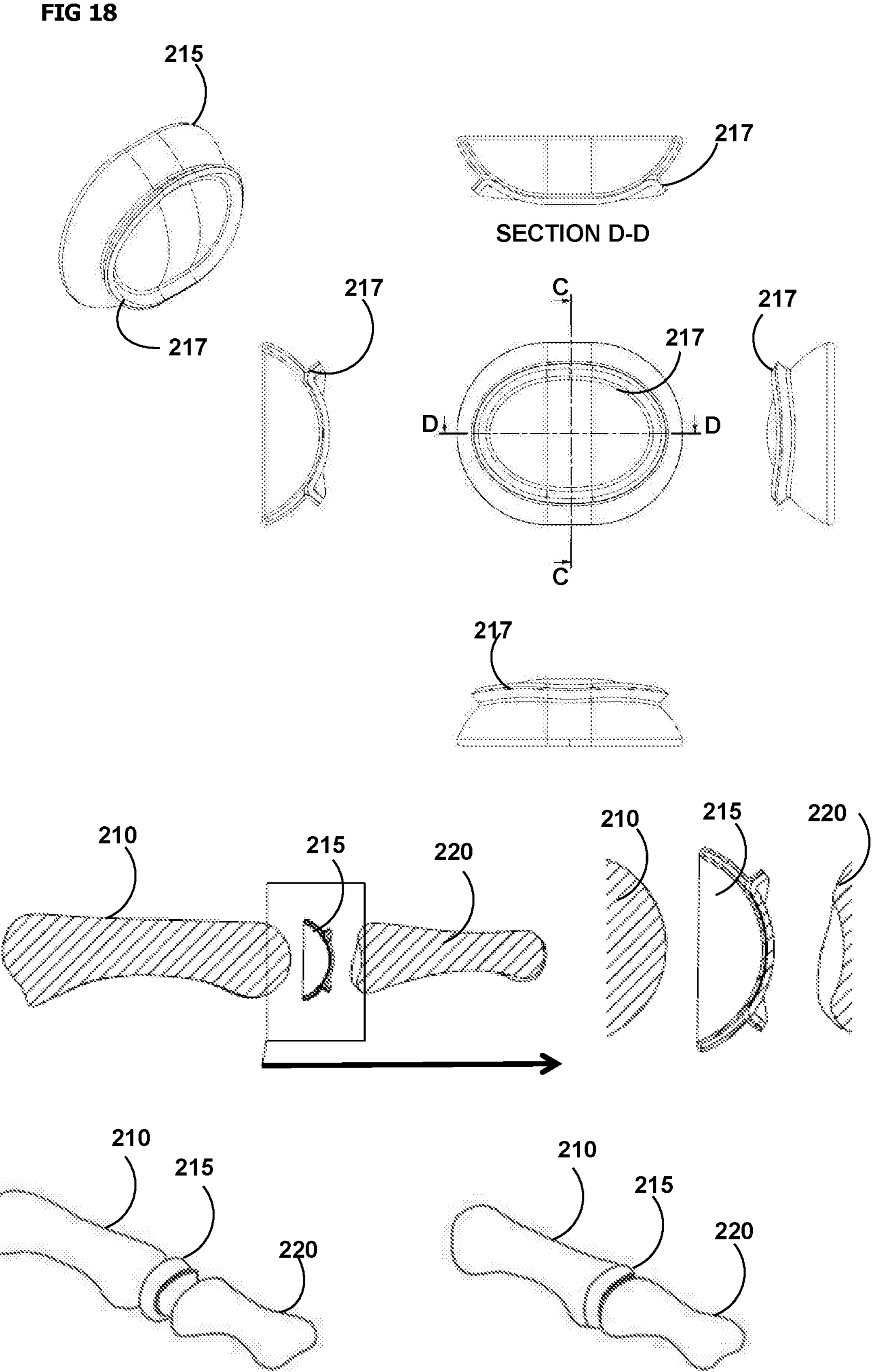

Aspects and embodiments of the present invention will now be described further, by way of example, with reference to the accompanying drawings, in which:

FIG. 1: FIG. 1A shows a view of the back section of the hinge joint implant having a hemi-spherocylindrical or spherocylindrical configuration, and FIGS. 1B and 1C depict three-dimensional views of the hinge joint implant having a capsule spherocylindrical before being squashed into a hemi-spherocylinder configuration;

FIG. 2: illustrates a hinge joint implant within a joint cavity between two joint components;

FIG. 3: is a view of the hinge joint implant having a hemi-spherocylindrical shape prior to implantation with a hollow centre;

FIG. 4: is a further illustration of a longitudinal cross-section of a hinge joint implant having a hemi-spherocylindrical configuration;

FIG. 5: FIG. 5A illustrates a hinge joint without an implant in place and then, and FIG. 5B shows a comparative hinge joint to FIG. 5A additionally with an implant in place;

FIG. 6: FIGS. 6A to 6D illustrate multiple front and back section views of a hinge joint implant, and with a sac and filler are also shown in FIGS. 6F and 6H;

FIG. 7: illustrates positioning of an implant within the joint cavity;

FIG. 8: illustrates multiple views of a hinge joint implant at different time points during flexion and extension of a simulated hinge joint;

FIG. 9: illustrates multiple front, back, and side views of joint components with which the invention interrelates;

FIG. 10: illustrates front, back, and side views of an embodiment of a capsule-shaped spherocylindrical implant;

FIG. 11: illustrates front, back, and side views of an embodiment of a capsule-shaped spherocylindrical implant wherein the implant is compressed/squashed;

FIG. 12: illustrates an example of a filler-filled capsule-implant;

FIG. 13: illustrates a double-implant in unsquashed and squashed (natural/deformed) spherocylindrical configuration;

FIG. 14: illustrates comparative configurations of the implant of the invention, specifically (A) a hemi-spherocylindrical; (B) a hemi-prolate spheroid; and (C) a spherical cap shape;

FIG. 15: illustrates various angles of flexion between the joint components when the implant is without a skirt and within the joint space between two joint components;

FIG. 16: illustrates various angles of flexion between the joint components when the implant is with a skirt and within the joint space and between two joint components;

FIG. 17: further illustrates how the dual thickness implant of the invention fits and functions between two joint components; and FIG. 18: illustrates the skirted implant and when it is between two articulating joint components.

As illustrated in FIGS. 1A, 1B and 1C, the implant 10 of the present invention can comprise a hemi-spherocylindrical or a spherocylindrical configuration. It will be understood that the implant is illustrated from a back section view in FIG. 1A and three-dimensional views in FIGS. 1B and 1C. It will also be understood that the Figure is not to scale and the thickness of implant is such that it can be inserted into a hinge joint. Further, it will be understood that the respective thicknesses of the sac layers and the filler may vary depending on the embodiment of the invention, for example when the filler is enclosed in a "sandwich" within the sac layers and the implant comprises a hollow concave space versus when the filler occupies the entire internal space of the implant and fills the capsule An exploded view of the implant 20 that extends beyond the joint cavity and located between two joint components which are two bone components 25 and 30 are illustrated in FIG. 2. The implant 20 may be of a consistent thickness throughout the implant or may have regions of different thicknesses, such as for example a dual thickness, or thicker or thinner in the central region (20*a*) than at the rim (20*b*). Initially, the implant 10 could be manufactured prior to creating the hemi-spherocylindrical configuration of the hinge joint implant 20 shown in FIG. 2. The joint components comprise for example, bones with/without cartilage 25 and 30. Generalised structures of the bones are shown to have either a concave 25 or a convex-end 30 surface. The implant 20 is shown to comprise a rim 20*b* and a central region 20*a*, and the curved ends of the implant 20 are shown to be configured such that they extend over the sides of the bone-end that has a convex-shape 30.

FIG. 3 is a three-dimensional representation of an example of a substantially hemi-spherocylindrical implant 20 of the present invention which comprises a concave region 22. The final shape of the implant will depend on the deformation in the joint during articulation. The concave region 22 can be suitably configured to extend over a joint component, for example a convex bone.

As illustrated in FIG. 4, a transverse cross section of an implant 40 embodying the present invention is shown which reveals the outer sac layer 42, and the filler 46 enclosed between the sac layers. The implant 40 is also shown to have a hollow centre. The sac 40 is made of suitable material, and a filler 42 made of suitable material and which is shown to be completely enclosed within the sac.

FIG. 5A depicts a representation of a hinge joint without an implant in which the joint component bones with/without cartilage 45 and 55 and ligaments 50 can be seen and FIG. 5B shows the hinge joint comprising an implant 60 embodying the invention, a convex bone 55 joint component, and a corresponding concave bone 45 joint component, wherein the ligaments 50 have not been compromised and remain intact. Thus, the minimally invasive implant 60 is another embodiment of the invention resulting in preservation of the ligaments during insertion into a patient. Thus the implant can be situated such that the ligaments 50 are not compromised. The hinge joint implant 60 is configured such that it fits within the joint cavity and the implant may extend over the ends of the convex bone with/without cartilage 55. FIG. 5B also shows the geometry and the kinematics of the implant 60 are controlled anatomically.

FIG. 6 illustrates a front, back, and side representations of an implant 70 embodying the invention in a state of motion between a convex bone with/without cartilage 65 and a concave bone with/without cartilage 75 as joint components. The implant 70 is positioned within the joint cavity and extending around the end of a joint component surface which is convex-shaped, for example bone and/or cartilage 65. The implant is shown in motion during flexion and extension of the hinge joint. FIGS. 6E to 6H additionally show side views of the implant 70 between bones 65 and 75 at the hinge joint during flexion and extension. The implant 70 comprising the sac 72 envelops a filler 74.

FIG. 7 illustrates an alternative embodiment of the implant of the invention 80 wherein the implant has a pre squashed spherocylindrical configuration and an outer sac layer and a filler that occupies or fills the entire implant. For example, the implant 80 is a gel-filled capsule. The implant 80 is shown in an exploded view at a joint cavity between joint components that are a convex bone with/without cartilage 85 and a concave bone with/without cartilage 90. It will be understood that the illustration is not to scale but represents the relative positioning of the implant between the joint components. As illustrated, the implant can fit entirely within the cavity and not extend around the sides of a joint component surface, such as bone with/without cartilage 85.

FIG. 8 represents another alternative embodiment wherein the implant of the invention 80 is shown to be located between joint components, a convex bone with/without cartilage 85 and a concave bone with/without cartilage 95, and functions through a caterpillar-track type motion and the implant 80 is shown to entirely fit within the joint cavity between the bones at the joint.

As is illustrated in FIG. 9, an implant of the invention 105 can comprise two separate pieces which are both spherocylindrical in configuration and when positioned under each of the condyles of the joint component bone with/without cartilage, for example between bones with/without cartilage 95 and 100 take on a deformed configuration 105*a*. The bones with/without cartilage 95 and 100 are provided with a two-piece implant 105 comprised of two pieces that are separate and optionally joined to each other, which have a spherocylindrical configuration and comprise a sac enveloping a filler. The implant 105 functions by improving hinge joint articulation by offering a caterpillar-track type motion.

FIG. 10 illustrates an implant of the invention 115 comprising an outer sac layer 117 and a filler 119 that completely occupies the internal space of the implant such that it fills the entire capsule. FIGS. 10D to 10F represent side-views of the same. FIG. 11 depicts the implant 115 positioned in an articulating two component joint. FIG. 11C illustrates the implant 115 having a deformed configuration and FIGS. 11D to 11F represent side-views of the same. The filler 117 comprises for example a gel, between the articulating joint components 110 and 120 at the hinge joint.

In one embodiment in FIG. 12 the implant can comprises a filler-filled capsule implant 135 which is gel-filled and with a substantially spherocylindrical configuration with an at least approximately cylindrical main body portion. The illustration is in an unsquashed spherocylindrical configuration 135 in FIG. 12A and in a squashed or slightly squashed spherocylindrical configuration 137 in FIG. 12B between the joint surface components 130 and 140, in which each component is for example a bone and/or cartilage in a hinge joint cavity. Bone 130 is shown to comprise a convex-end surface.

In an alternative embodiment in FIG. 13A the implant can take the form of at least a pair of implant members of substantially spherocylindrical configuration 150, although truncated with respect to the embodiment of FIG. 12, and which in one embodiment can approximate to a near oval or spherical shape/configuration. Once in location for use during joint articulation the pair of implant members adopt compressed/deformed configuration 155 as illustrated in FIG. 13B and squashed/compressed/deformed between the joint surface components 145 and 160, in which each component is for example a bone and/or cartilage in a hinge joint cavity. The bone 145 as illustrated comprises condyles.

As shown in FIG. 14, the implant with a (A) hemi-spherocylinder, (B) hemi-prolate spheroid, or (C) spherical cap shape is squashed to produce a caterpillar motion to simulate movement in a hinge joint. This geometry would be very suitable for small joints that are of a hinge configuration such as the metacarpophalangeal (MCP) proximal interphalangeal (PIP) and distal interphalangeal (DIP) joints.

In one embodiment, as shown in FIG. 15, the implant 215 *f* the invention can have a dual thickness which permits joint articulation between the two joint components 210 and 220 and as an example of an implant with regions of different thickness as discussed in detail above The implant is shown to facilitate various angles of flexion such as 0° and 70°. The implant is also shown to have a localised thicker region (217) in the load bearing area, and lubricant reservoirs 218 thereby formed at the extremities of the implant 215.

FIG. 16 represents an embodiment of the implant of the invention 215 comprising a flange or skirt formation 217 on the implant. FIGS. 16A to 16C show how the implant with a flange/skirt formation 217 functions between the two joint components 210 and 220 during articulation. The flange/skirt 217 can serve to locate and/or assist the retention of the implant in position relative to the adjacent bone. Any form of connection/fixture arrangement to the bone can also be provided by way of the flange/skirt 217. Specifically, FIG. 16A shows the skirt-bearing implant positioned between the joint components 210 and 220 when the angle of flexion is 0°, whereas FIG. 16B illustrates how the skirted implant 215 facilitates movement of the joint components 210 and 220 when the angle of flexion is 70°.

FIG. 17 further represents an embodiment of the implant of the invention 230 comprising a dual thickness fits between the joint components 210 and 220. FIG. 17A illustrates the dual thickness implant 230 with a thicker middle region and thinner extremities which is shaped to fit around the sides of the convex joint component 210, and how that would work during flexion wherein the angle is >0°. FIG. 17B illustrates the dual thickness implant 230 in situ between the joint components 210 and 220, wherein the angle of flexion is 0°.

In a specific embodiment, the implant of the invention comprises a flange/skirt 217 as illustrated in FIG. 18. Several views of the implant 215 comprising a skirt 217 are shown in FIG. 18. The skirted implant is also shown between two joint components 210 and 220. The height to-which the skirt/flange 217 employed in any embodiment of the invention extends from the body of the implant 215 can advantageously be in the order of 1 mm. As illustrated, the flange/skirt can also be provided at the point of connection of two pieces of a multi-piece implant. The joint can be formed by any suitable process including laser-welding. Also, although not illustrated, the flange/skirt can exhibit lug or ear portion extending a yet greater distance from the implant 215 body. Such distance can be in the range 2 mm to 10 mm, and particularly in the order of 5 mm. These lugs/ears can advantageously further assist with the locating and securing of the implant relative to the adjoining bone of the joint.

The invention claimed is:

1. A hinge joint implant for an articulating two-component hinge joint, the implant comprising:

i) a sac formed of deformable material and comprising an outer layer; and ii) a filler inside the sac;

wherein, the implant comprises a spherocylindrical configuration when in a non-compressed condition, and comprises a deformed spherocylindrical configuration comprising a substantially hemi-spherocylindrical configuration when in a compressed condition by being located in situ within a joint cavity defined by the articulating two-component hinge joint, and wherein the filler comprises a material with a coefficient of friction that allows opposite sides of the sac to move relative to one another when a force is applied to the joint, and an outer surface of the sac is arranged not to move relative to the naturally occurring joint component surface it is in contact with, during articulation, and wherein the amount of filler material is just sufficient to allow the relative movement within the sac.

2. An implant as claimed in claim 1, wherein the outer surface of the sac arranged not to move relative to the joint component surface does not move relative to the joint component surface at least partially due to the group consisting of: coefficient of friction during articulation, an adhesive, a mechanical fixture, a localised biological fixation, and combinations thereof.

3. An implant as claimed in claim 1, wherein the deformed spherocylindrical configuration comprises a substantially squashed spherocylindrical configuration or comprises a substantially hollow spherocylindrical configuration.

4. An implant as claimed in claim 1 comprising a discrete pair of filler-filled implants, and arranged such that each of the pair of filler-filled implants is arranged to be deformed by a respective condyles of the joint components.

5. An implant according to claim 1, wherein the sac includes an adhesive or mechanical fixture.

6. An implant according to claim 1, wherein the implant comprises a thickness from about 0.01 mm to about 1.5 mm or from about 0.05 mm to about 0.8 mm.

7. An implant according to claim 1, for inserting into a hinge joint in a hand, ankle, elbow, thumb, finger, or toe, optionally wherein when the hinge joint is in a finger, the hinge joint is an interphalangeal joint comprising at least one of a distal interphalangeal joint (DIP) and a proximal interphalangeal joint (PIP).

8. An implant according to claim 1, wherein the sac comprises a polymer, optionally wherein the elastomeric polymer is selected from: polyhydroxyalkanoates, polycarbonate urethanes, polyurethane, urethane, silicones, polycarbonate urethane based silicones, and those based on cellulose.

9. An implant according to claim 1, comprising an external surface roughness or a coating to at least one of provide friction and act as an adhesive.

10. An implant according to claim 1, wherein the outer surface of the sac is coated with a coating material, and at least one of the coating material and the filler material facilitates at least one of bone and cartilage repair, optionally wherein the coating material is pharmaceutically active.

11. An implant according to claim 1 wherein the filler material comprises a phospholipid, an elastomer, a gel, a hyaluronic acid based hydrogel, a natural polymer, and/or an alginate-based hydrogel.

12. An implant according to claim 1, having regions of different wall thickness comprising a dual thickness wall, with a localized region of increased thickness at a load-bearing region, wherein an edge of the load-bearing region serves to help define a fluid reservoir region within the implant.

13. An implant according to claim 1 and including an engagement formation for assisting with at least one of locating and securing the insert to a bone of the joint, wherein the engagement formation is arranged to be provided on a convex portion of the insert, and comprises a flange or skirt extending from a main body of the insert, and optionally wherein the engagement formation includes lug formations, optionally wherein the lug formations extend in the range 2 mm to 10 mm from the main body of the insert.

14. A method of locating the implant of claim 1 within a hinge joint cavity including manipulating joint components and associated ligaments of the hinge joint and subsequently allowing the joint components to compress the implant for articulated movement of the joint.

15. A method as claimed in claim 14, wherein the implant during location, and after subsequent compression, maintains a substantially hemi-spherocylindrical configuration.

16. A method as claimed in claim 14, wherein the implant is retained in location at least partially by an adhesive material between the outer surface of the implant and the surface of the joint components, and wherein the adhesive material is delivered while the implant is in situ, optionally wherein the adhesive material is delivered by way of a bore provided through the joint component and opening beneath the surface of the in situ implant.

17. A method of treating or prophylaxis of a disease or condition in which the hinge joint is indicated in a patient in need thereof, comprising administering the implant according to claim 1, optionally wherein the disease or condition is at least one of arthritis, and torn or damaged cartilage.

18. A method for forming the implant according to claim 1 from two or more pieces that are subsequently welded together.

* * * * *